United States Patent
Bhattacharya et al.

(10) Patent No.: US 8,747,637 B2
(45) Date of Patent: Jun. 10, 2014

(54) AGAROSE NANO-PLATINUM COMPOSITE

(76) Inventors: Shantanu Bhattacharya, New Delhi (IN); Shubhra Gangopadhyay, Columbia, MO (US); Keshab Gangopedhyay, Columbia, MO (US); Nripen Chanda, Columbia, MO (US); Paul Sharp, Columbia, MO (US)

( * ) Notice: Subject to any disclaimer, the term of this patent is extended or adjusted under 35 U.S.C. 154(b) by 1170 days.

(21) Appl. No.: 12/170,287

(22) Filed: Jul. 9, 2008

(65) Prior Publication Data
US 2009/0014333 A1 Jan. 15, 2009

Related U.S. Application Data

(60) Provisional application No. 60/958,743, filed on Jul. 9, 2007.

(51) Int. Cl.
*C07K 1/26* (2006.01)
*B01D 57/02* (2006.01)
*H01B 1/22* (2006.01)
*G01N 27/447* (2006.01)

(52) U.S. Cl.
CPC .... *G01N 27/44747* (2013.01); *G01N 27/44704* (2013.01)
USPC ............ 204/456; 204/450; 204/469; 204/470

(58) Field of Classification Search
USPC ................. 204/450, 456, 469, 470, 616, 563; 252/500, 512, 514
See application file for complete search history.

(56) References Cited

U.S. PATENT DOCUMENTS

| 5,143,646 A * | 9/1992 | Nochumson et al. ......... 204/469 |
| 2003/0205473 A1 * | 11/2003 | Liu et al. ...................... 204/456 |
| 2005/0109620 A1 * | 5/2005 | Kern et al. .................... 204/450 |

FOREIGN PATENT DOCUMENTS

CN 1966719 A * 5/2007

OTHER PUBLICATIONS

Bhattacharya, A Novel PCR Based DNA Microanalyzer System for Detection of Viral Genome, Ph.D. Dissertation Publication Date Aug. 2006.*

(Continued)

*Primary Examiner* — Luan Van
*Assistant Examiner* — Steven Rosenwald
(74) *Attorney, Agent, or Firm* — Polsinelli PC

(57) ABSTRACT

The invention relates to compositions and methods of using electrophoresis separation matrices. The invention provides nano-particle comprising separation matrices having increased conductivity at low voltage.

3 Claims, 21 Drawing Sheets

(56) References Cited

OTHER PUBLICATIONS

Wang et al. Chem. Commun., 2007, 3060-3062 First published as an Advance Article on the web Jun. 28, 2007.*
Zhou et al. Journal of Nanoparticle Research 3: 379-383, 2001 Publication Date: Dec. 1, 2001.*
Material Safety Data Sheet, Sigma-Aldrich product 482315 platinum (II) chloride Revision Date Mar. 13, 2010.*
Solid State Ionics vol. 147, Issues 3-4, Apr. 2002, pp. 281-287.*
Nano Lett., vol. 3, No. 1, Published on Web Dec. 3, 2002.*
RNA Isolation and Analysis, BIOS Scientific Publishers (1994).*
Huang et al. Electrophoresis, 2003, 24, 2896-2902.*
Nakao J. Coll. Sci., 171, 1995, 386-391.*
Bocek et al. Electrophoresis, 1992, 13, 31-34.*
Cohen, A.S., et al, Rapid Separation and Purification of Oligonucleotides by High-Performance Capillary Gel Electrophoresis, Proc. Natl. Acad. Sci. USA, Dec. 1988, p. 9660-9663, vol. 85.
Bard, Allen, et al, Electrochemical Methods Fundamentals and Applications, 1980, John Wiley and Sons, New York.
Hawcroft, David, The Electrophoresis of Nucleic Acids, Electrophoresis, 1997, chapter 5, p. 66-83, IRL Press at Oxford.
Fu, Lung-Ming, et al, Low Voltage Driven Control in Electrophoresis Microchips by Traveling Electric Field, Electrophoresis, 2003, p. 1253-1260, 24.
Muszynska, Monika, et al, Composite Polymeric Electrolytes Based on Poly(Ethylene Oxide) Matrix and Metallic Aluminum Filler, 2002, p. 281-287, 147.
Morita, Masayuki, et al, Ionic Conductance of Composite Electrolytes Based on Network Polymer With Ceramic Powder, Solid State Ionics, 2006, p. 715-720, 177.
Chen, Sihai, et al, Synthesis of Thiolate-Stabilized Platinum Nanoparticles in Protolytic Solvents as Isolable Colloids, J. Phys. Chem., 2001, p. 5397-5403, 105.
Ingelsten, Hanna, et al, Kinetics of the Formation of Nano-Sized Platinum Particles in Water-in-oil Microemulsions, Journal of Colloid and Interface Science, 2001, p. 104-111, 241.
Naka, Kensuke, et al, Synthesis of Nanocomposite of Metal Nanoparticles Utilizing Miscible Polymers, Polymer Bulletin, 2004, p. 171-176, 52, Springer-Verlag.
Stellwagen, Earle, et al, The Free Solution Mobility of DNA in Tris-Acetate-EDTA Buffers of Different Concentrations, with and without Added NaCl, Electrophoresis, 2002, p. 1935-1941, 23, Iowa City, Iowa, USA.
Hong, Jong Wook, et al, Microfabricated Polymer Chip for Capillry Gel Electrophoresis, Biotechnol. Prog., 2001,p. 958-962, 17.
Duffy, David, et al, Rapid Prototyping of Microfluidic Systems in Poly(dimethylsiloxane), Anal. Chem., 1998, p. 4974-4984, 70.
Kundu, T.K., et al, Nanocomposites of Lead-Zirconate-Titanate Glass Ceramics and Metallic Silver, 2001,p. 2732-2734.
Bookeun, Oh, et al, Preparation of UV Curable Gel Polymer Electrolytes and their Electrochemical Properties, Bulletin of the Korean Chemical Society, 2002, p. 683-687, 23(5).
Wieczorek, W., et al, Composite Polyether Based Solid Electrolytes, 1995.

\* cited by examiner

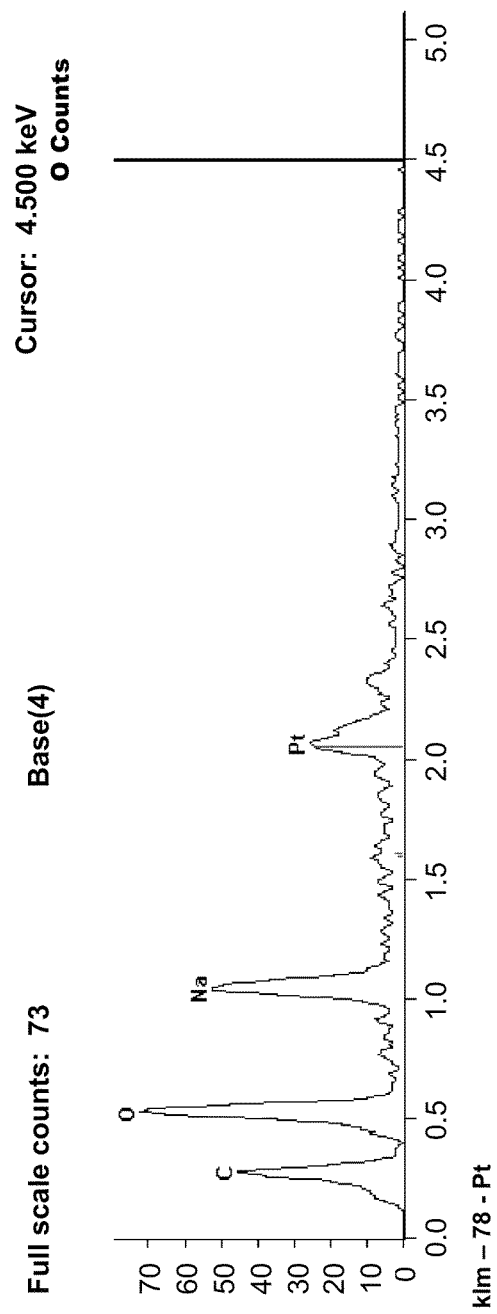

FIG. 7

| Type of agarose | Time =10mins | Time= 15mins. | Time= 20mins. | Time= 25mins. |
|---|---|---|---|---|
| Undoped | 7.8mm | 13.4mm | 18.7mm | 24.7mm |
| Doped | 13.1mm | 19.4mm | 27.8mm | 36.6mm |

FIG. 12

| Type of Material | $R_s$(Ohm) | $C_{di}$ | $R_{ser}$ |
|---|---|---|---|
| Plain Agarose | 98 | 1.64 | 1.00E-7 |
| | 96.4 | 1.88 | 1.00E-7 |
| | 97.3 | 1.79 | 1.00E-7 |
| Average | 97.2 | 1.77 | 1.00E-7 |
| Std. Dev. | 0.8 | .12 | 0 |
| Agarose doped with 5.8 mM Platinum Hydrosol | 70.4 | 1.9 | 1.00E-7 |
| | 69.7 | 2.09 | 1.00E-7 |
| | 69.0 | 2.12 | 1.00E-7 |
| Average | 69.7 | 2.04 | 1.00E-7 |
| Std. Dev. | .07 | .12 | 0 |
| Agarose doped with 11.6 mM Platinum Hydrosol | 61.5 | 2.39 | 1.00E-7 |
| | 60.4 | 2.35 | 1.00E-7 |
| | 60.5 | 2.38 | 1.00E-7 |
| Average | 60.8 | 2.37 | 1.00E-7 |
| Std. Dev. | .061 | .21 | 0 |

FIG. 17
FIG. 17A
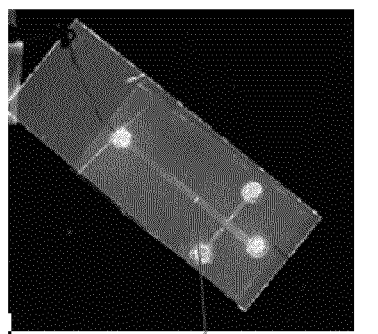
FIG. 17C
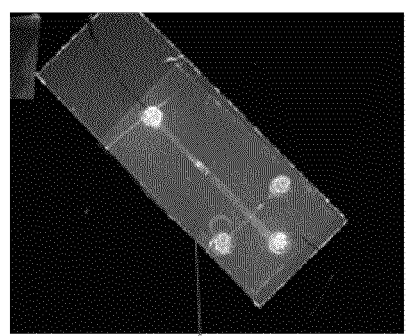
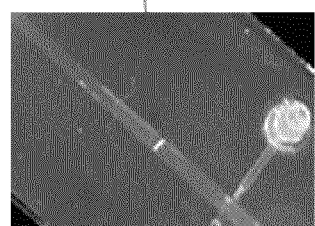
FIG. 17B
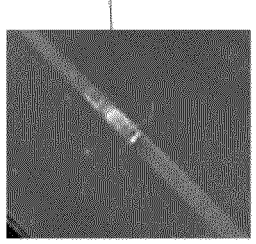
FIG. 17D FIG. 18
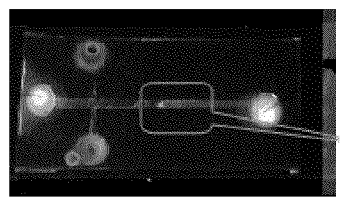 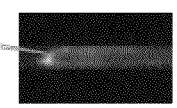 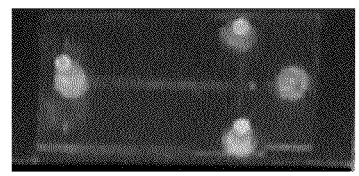
FIG. 18A  FIG. 18B  FIG. 18C
FIG. 18D

US 8,747,637 B2

AGAROSE NANO-PLATINUM COMPOSITE

RELATED APPLICATIONS

This patent application claims priority from U.S. provisional patent application Ser. No. 60/958,743, filed Jul. 9, 2007, entitled "Agarose Nano-Platinum Composite", and which is incorporated herein by reference in its entirety.

FIELD OF THE INVENTION

The present invention relates to any gel composition, whereby the gel composition includes any material that is conductive in nature and has the ability to transfer a charge. More particularly, the present invention relates to separation matrices containing nano-particle additives that enhance conductivity as for micro-channel electrophoretic separation systems.

BACKGROUND OF THE INVENTION

Technologies to enable miniaturized DNA electrophoresis within fused silica capillaries (50-75 microns ID) have been under development over the last two decades. The large surface area to volume ratio in micron-sized capillaries leads to an effective loss of the resistive Joule heat, allowing the voltage limitations that are imposed in slab gel electrophoresis to be surpassed. Also implicated is the need to use higher electric fields to achieve higher DNA separation speeds in micro-channel systems. The development of DNA separation matrices for capillary electrophoresis systems remains an important endeavor, as the properties of the sieving polymers directly dictate the separation resolution and the migration behavior of DNA molecules, as well as the difficulty or ease of micro-channel loading of the matrix. Some of the commonly used matrices include agarose, polyacrylamide, hydroxyalkylcellulose [6], polyvinyl alcohol and its copolymers.

There is a tremendous emphasis on research to provide micro-fluidic integrated gene analysis systems with sample preparation and analysis processes on a single micro-fabricated substrate. Such systems demonstrate an overall reduction in size, reduced use of reagents, increased speed and accuracy of analysis, and increased portability for field use. The field applications of such devices, however, are limited by power requirements imposed by the highly resistive capillary columns. The typically applied DC voltages to gel filled micro-fabricated capillaries in order to execute electrophoresis run in several kilovolts (1-3 KV) which can be only achieved in a laboratory setup. For example, DNA separation generally requires electric field strength of 300-800 V/cm and an applied voltage of the order of 1-3 KV in electrophoresis applications. Therefore, there is a need for developing a novel class of matrices with increased conductivity, which enhances sample (i.e., a DNA charged on the matrix) mobility while retaining resolution.

SUMMARY OF THE INVENTION

The present invention relates to any gel composition, whereby the gel composition includes any material that is conductive in nature and transfers a charge. It is an object of the present invention to provide a novel separation matrix that enables electrophoresis at a relatively low voltage. Specifically, the invention is a composition including a separation matrix and nano-particles that has a higher conductive capacity compared to the separation matrix alone. Suitable separation matrices include agarose, polyacrylamide, hydroxyalkylcellulose, polyvinyl alcohol, and other matrices known in the art. In one embodiment of the invention, the conductive matrix composite comprises agarose, a buffer, and a nano-particle hydrosol. A suitable amount of agarose includes, but is not limited to, a weight concentration of about 0.25, 0.3, 0.4, 0.5, 0.6, 0.7, 0.8, 0.9, 1.0, 1.25, 1.5, 1.75, 2.0, 2.25, 2.5, and 2.75 or more percent.

A suitable buffer includes those commonly used in the art for electrophoresis. Exemplary buffers include Tris based buffers such as Tris-borate EDTA (TBE) and Tris-acetate-EDTA (TAE) buffer. Preferably, TAE may be used with the invention. More preferably, TAE having a pH of about 8.0, 8.2, 8.4, and 8.6 or more may be used with the invention.

As used herein, the term "nano-particle" refers to a single particle having a size of less than about 400 nm. Preferably, the nano-particle has a size that is less than about 100 nm. Nano-particles may form aggregates that are less than 400, 350, 300, 275, 250, 225, 200, 150, 100, and 50 nm or less. A suitable nano-particle size ranges from about 0.5 nm to about 30 nm. More preferably, the particle sizes range from about 3 nm to about 23 nm. More preferably, the particle sizes range from about 5 nm to 19 nm. More preferably the particle sizes are about 7.75, 8.0, 8.25 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 12.8, 12.9, 13.0, 13.1, 13.2, 13.3, 13.4, 13.5, 13.75, 14.0, 14.25, 14.5, 14.75, 15.0, 15.25, 15.5, 15.75, 16.0, 16.25, 16.5, 16.75, 17.0, and 17.5 nm.

A suitable nano-particle material may be formed from any conductive material. A suitable conductive material may include any metal or polymer. For example, a suitable metal includes copper, ruthenium, rhodium, palladium, silver, rhenium, osmium, iridium, platinum, gold, and mercury. In one embodiment, the nanoparticle material is platinum. By way of example, a suitable polymer includes polystyrene and silica. Further, the invention includes a combination of nano-particle materials to enhance or decrease nucleic acid mobility. More than one metal nano-particle may be combined, more than one polymer nano-particle may be combined, and at least one metal nano-particle and one polymer nano-particle may be combined.

As used herein, the term "hydrosol" refers to microscopic particles suspended in a liquid. The nano-particles of the invention may be suspended in a buffer or some other aqueous solution that enables the nano-particles to be dispersed throughout the separation matrix. A suitable amount of platinum hydrosol used with the invention ranges from about 0.5 mM to about 14.0 mM. Preferably, the amount of platinum hydrosol used is 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, and about 14.5 mM. More preferably, the amount of platinum hydrosol used is 4.0, 4.5, 5.0, 5.5, 5.8, 6.0, 6.5, 7.0, 7.5, 8.0, 8.5, 9.0, 9.5, 10.0, 10.5, 11.0, 11.5, 11.6 12.0, and 12.5 mM.

An objective of the invention is a gel composition having a dielectric constant above that of the separation matrix alone. Preferably, the dielectric constant of the gel composition is above the dielectric constant of the nano-particle. For example, when the gel composition includes agarose and platinum nano-particles, a suitable dielectric constant would be more than 13.4. Preferably, the dielectric constant is about 13.5, 13.8, 14, 14.5, 15, 15.5, 16, 16.5, 17, 17.5, 18, 18.5, 19, 19.2, 19.5, 20, 20.5, and 30 or more. More preferably, the dielectric constant is about 19.2.

Another objective of the invention is a method of making a conductive matrix for separating nucleic acids at a low voltage. The method includes mixing a nano-particle dispersion in a buffer resulting in a nano-buffer suspension; mixing agarose powder in the nano-buffer suspension; and, heating the agarose-nano-buffer suspension until the agarose gel is melted and later gelled. A low voltage includes an electric field strength that is less than about 500 V/cm. Preferably, the electric field strength is less than about 450, 425, 400, 350, 325, 300, 200, 150, or 100 V/cm.

It is another objective of the present invention to provide a method of making a conductive matrix for performing capillary electrophoresis at low voltage. The method includes mixing a nano-particle dispersion in a buffer resulting in a nano-buffer suspension; mixing agarose powder in the nano-buffer suspension; and, heating the agarose-nano-buffer suspension until the agarose gel is melted and later gelled. A low voltage includes an electric field strength that is less than about 500 V/cm. Preferably, the electric field strength is less than about 450, 425, 400, 350, 325, 300, 200, 150, or 100 V/cm.

BRIEF DESCRIPTION OF THE DRAWINGS

FIG. 2B is an EDS spectra of the inventive agarose-platinum composite, according to one embodiment.

FIG. 7 shows images of the fluorescent band of DNA separations on the agarose gel and the agarose-platinum gel fake at different times at 200 V.

FIG. 12 is a summary of the parameters generated from the curve fit (values, averages and standard deviations).

FIG. 13 graphically illustrates the comparison of gel dielectric capacitance and resistance.

FIG. 16B shows the placement of the separation microchannels. After being exposed to oxygen plasma (FIG. 16B), the mold containing the microchannels was sealed to another clear glass substrate (FIG. 16C). The microchannels were molded to a taper of 500 µm to an inch (FIG. 16D). FIG. 16E depicts the mold filled with agarose. FIGS. 16F and 16G shows the cross microchannels used to inject DNA sample orthogonally (A-B) into the main separation capillary (C-D).

FIG. 17 depicts the movement of a 100-1000 base pair gene marker through platinum doped agarose gels. FIG. 17A shows the movement of the marker captured in an UV detection setup after 25 seconds and FIG. 17B shows a magnified view of the marker. FIG. 17C shows the electrophoresis of the marker between 45 and 50 seconds and FIG. 17D shows a magnified view of the marker. (300 V DC was applied).

FIG. 18 shows the capillary electrophoresis of a 750 base pair nucleic acid segment in pure agarose (300V) (FIG. 18A), magnified view of the marker in pure agarose (FIG. 18B), in agarose with filler nano-particles (65V, electric field=25V/cm) (FIG. 18C), and in agarose with filler nano-particles with electrode polarity reversed (65V, electric field=25V/cm) (FIG. 18D).

DETAILED DESCRIPTION OF THE INVENTION

Figure 1A:
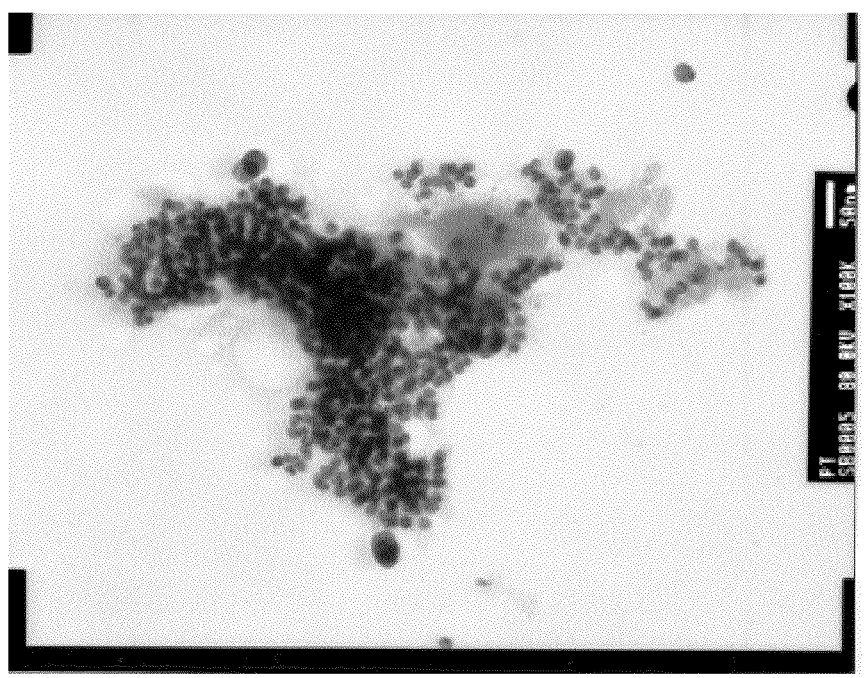
FIG. 1A is a TEM image of the spherical platinum nano-particles on a copper grid.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

The present invention provides a novel gel material with enhanced conductivity for capillary electrophoresis at a low voltage by doping a separation matrix with nano-particles. The inventive gel material comprises at least one nano-particle. Preferably, the gel material comprises more than one nano-particle.

The invention also includes a novel gel material having enhanced conductivity that includes 1) a separation matrix, 2) electrophoresis buffer, and 3) a nano-particle hydrosol with particle sizes ranging from about 0 nm to about 400 nm. Preferably, the nano-particle hydrosol includes particle sizes ranging from about 1 nm to about 100 nm. More preferably, the nano-particle hydrosol includes particle sizes ranging from about 2 nm to about 50 nm. More preferably, the nano-particle sizes range from about 3 nm to about 25 nm.

The nano-particle material may be formed from any metal or polymer. For example, a metal nano-particle may be formed from a metal such as copper, ruthenium, rhodium, palladium, silver, rhenium, osmium, iridium, platinum, gold, and mercury. The nano-particle may also be formed from a polymer including, but not limited to, polystyrene and silica. Preferably, the nano-particle material is formed from platinum. The invention also contemplates using a combination or mixture of nano-particle materials. Preferably, the nano-particle hydrosol includes at least one metal nano-particle. The nano-particle hydrosol may include at least one polymer nano-particle. Furthermore, the nano-particle hydrosol may include at least one polymer nano-particle and at least one metallic nano-particle. One skilled in the art may recognize that a polymer nano-particle may have a reverse effect on the conductivity of the separation matrix resulting in a decrease in nucleic acid mobility.

According to one embodiment, platinum hydrosols are employed as the nano-particles. The platinum hydrosols may be prepared by a reduction of potassium platinum (II) tetrachloride by sodium boro-hydride in surfactant micelles by methods commonly known in the art. Preferably, the mean diameter of the nano-particles is calculated to be about 13.16±3.93 nm using a platinum to surfactant ratio of about 0.46. A skilled artisan will recognize that the sizes of the nano-particles may be varied by changing the concentration of the reducing agent (sodium borohydride) with respect to the chloro-platinate salt solution and also the surfactant, such as mercaptosuccinic acid.

The nano-particle containing separation matrix may be prepared using agarose. Other separation matrices include polyacrylamide, hydroxyalkylcellulose, polyvinyl alcohol and other matrices commonly known in the art. By way of example, the nano-particle containing separation matrix may be prepared by microwave heating of the agarose powder in a solution of 1×TAE buffer and the nano-platinum dispersion mixed in a 1:4 volumetric ratio. The volumetric ratio may also include 1:1, 1:2, 1:3, 1:5, 1:6, 1:7, 1:8, and more.

The Bergemen model, as described in the article T. K. Kundu, D. Chakravorty, "Nano-composites of lead-zirconate-titanate glass ceramics and metallic silver", *Applied Physics Letters*, Vol. 67, pp. 2732-2734, 1995, may be employed to calculate the volume fraction of the dispersed platinum nano-particles using the following equation:

$$\varepsilon = \phi^2 \varepsilon_m + (1-\phi)^2 \varepsilon_g + 2\phi(1-\phi)\left(\frac{1}{\varepsilon_g} - \frac{1}{\varepsilon_m}\right)\ln\left(\frac{\varepsilon_m}{\varepsilon_g}\right)$$

Where, $\varepsilon_m$ is the magnitude of the dielectric constant of the dispersed platinum phase, $\varepsilon_g$ is the dielectric constant of the agarose, $\emptyset$, is the volume fraction of the dispersed phase and $\varepsilon$ is the dielectric constant of the composite. The volume fraction can be estimated by plugging in the values of the dielectric constant of platinum (13.4), agarose (2.4) and the composite material (19.2). The volume fraction is calculated to be above unity, which explains that the inventive composite does not behave as a bulk material.

The invention also provides a method for preparing the agarose nano-particle gel composite by doping the agarose with a predetermined nano-particle. The inventive process includes the steps of 1) mixing nano-particle dispersion in a gel buffer comprising TAE, whereby resulting in a nano-buffer suspension, 2) mixing agarose powder at approximate 2% in weight in the nano-buffer suspension, whereby resulting in an agarose-nano-buffer suspension, and 3) heating the agarose-nano-buffer suspension at approximate 80° C. until agarose gel is melted. According to one embodiment of the inventive method, platinum hydrosols are employed as the nano-particle dispersion at an approximate 1:4 volumetric ratio against the TAE gel buffer solution, whereby retaining a pH between approximate 8.4 to approximate 8.6.

The invention also provides a method of using the agarose-nano-particle gel composite with capillary electrophoresis to increase nucleic acid mobility at low voltage. The improvement over the current capillary electrophoresis technique comprises employing an agarose-nano-particle gel composite, a gel buffer comprising TAE with a pH of from approximate 8.4 to approximate 8.6, a well buffer, since the DNA mobility is found to be the best for pH values in the same range, and a potential of from about 300 volts (V) to about 65 volts.

According to one embodiment of the invention, agarose-platinum gel composite is employed and enhancements in sample DNA's mobility at low voltages are observed.

While the invention has been described in connection with specific embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

EXAMPLES

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of non-critical parameters that could be changed or modified to yield essentially similar results.

Methods

Nanoparticle Preparation

Platinum nano-particle hydrosols at two different concentrations were prepared by reducing an aqueous solution of potassium platinum (II) tetrachloride ($K_2PtCl_4$, 5.8 mM and 11.6 mM) with sodium borohydride (137.2 mM and 274.4 mM) in the presence of mercapto succinic acid (MSA, 26.7 mM and 53.4 mM) in a Schlenk flask under an argon atmosphere. For both concentrations the molar ratio of MSA and $K_2PtCl_4$ was 0.46 (S/Pt). The formation of the platinum hydrosol was monitored by observing a change in coloration. Both hydrosols were analyzed with a Shimadzu UV-Vis spectrophotometer to confirm the presence and sizes of platinum nano-particles (sharp peak at 220 nm). A JOEL 1200 EX transmission electron microscope (TEM) was used to further characterize the size of the particles. The mean particle size and size distribution were obtained from the digitized photo images using Adobe Photoshop software. Each platinum hydrosol solution was separately mixed with 1×TAE (Triacetate buffer, pH=8.4, M/S Fisher BioReagents) buffer sample in 1:4 volume ratio. Molecular biology grade low EEO (electro-endosmotic flow) agarose was mixed with this solution to give a 2% (weight/vol) gel after heating the mixture to 80° C. followed by cooling to room temperature.

Conductivity Analysis

Conductivity measurements of the doped and undoped agarose gels were performed using a micromanipulator probe station. Thoroughly cleaned glass slides were sputter coated with two 1 cm×1 cm square disjointed platinum electrodes separated by 1000 microns (130 nm thick) using metallization and liftoff techniques commonly known in the art. A micromanipulator probe station was connected to a Lab-View based data acquisition system (DAQ, M/S National Instruments). A thin layer of the agarose gel with and without the nano-particle solution was spun bridging the two disjointed platinum electrodes and the current-voltage (I-V) data was acquired (0-20 V range). Subsequently, a plot between the current density and electric field was obtained. The I-V characteristics remained linear between 0-15 V, after which the agarose started to melt. The corresponding field value at this melting point was approximately 100-120 V/cm.

The dielectric constant of the inventive agarose-platinum composite was also measured against that of the agarose gel. During the measurements, the CV measurements were performed on the different films spun coated on p+(0.0030-0.0070 Ω-cm) Si substrates using a HP 4284A LCR meter. The Ti top contacts were electron beam evaporated and patterned using a shadow mask. The film thicknesses were measured with an alpha-step 200 profilo-meter (M/s Tencor Instruments). The dielectric constants were determined for the fully dried and wetted films for both doped (i.e., inventive agarose-platinum) and plain agarose.

Electrophoresis

Slab gel electrophoresis was conducted with and without platinum hydrosol wherein a 527 bp amplified [PCR based] viral DNA sample was driven through these gels at identical voltages. A digital image was acquired on a Kodak inverted camera after 10, 15, and 20 minute intervals at voltages ranging from 50-200 V and a comparison of DNA mobility in both gel materials was performed (FIG. 7).

Impedence Analysis of Doped Gel Material

Figure 11:
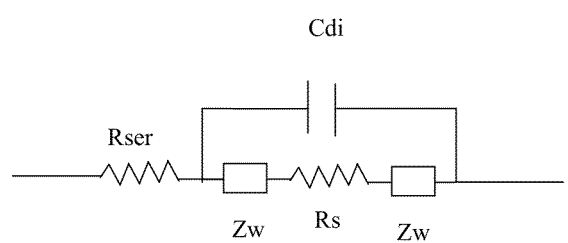
FIG. 11 illustrates a circuit model used for analysis.

The gel dielectric constants and resistance were measured using impedance spectroscopy techniques wherein a set of interdigitated micro-fabricated Pt electrodes over a silicon wafer were used to determine the impedance of the medium. The electrodes were connected to two bond pads over which micro-manipulator probe tips were used to measure the impedance over a frequency range of 100 Hz-100 KHz using an Agilent 4284A precision LCR meter with a Lab View interface. The electrodes had a width of about 17 μm and were spaced at 23 μm. A PDMS (polydimethyl siloxane) well was further mounted for containing and correctly positioning the gel melt over the set of electrodes. After the gel solidified, the impedance and phase angle were generated and plotted on a logarithmic scale. A normalization of the system was done by measuring the impedance of deionized water between any two experiments for baseline correction purposes. A fairly simple circuit model of a pair of electrodes immersed in an electrolytic solution is shown in FIG. 11 where $C_{di}$ is the dielectric capacitance (it contains dielectric contributions from all material surrounding the electrodes, including the gel), $R_s$ is the bulk solution resistance (charge transport across the bulk gel), and $Z_w$ is the interfacial impedance, which accounts for the changes in the ionic gradient at the interface and depends mostly on properties of the electrolytes and electrodes. $R_{ser}$ is the series resistance due to the physical shape of the electrodes, the inter-electrode spacing, etc. Each circuit component represents either a physical structure or a factor that affects the measurement. The circuit is modeled mathematically wherein extractions of parameters start with a first estimate of each parameter in the model. By iterating each of these parameters the predicted and experimental data points were fitted while minimizing the least square error to a tolerance value of $10^{-13}$. When the error values were reached the fitting was terminated and the final values of the parameters were extracted and recorded. FIG. 12 represents the extracted parameters, with their averages and standard deviations for each trial. A thin film of the doped gel was prepared by spin-coating the molten gel onto a plain silicon substrate, which was then heated in a vacuum oven (at 60° C. overnight). The silicon substrate with the dried composite film was characterized using a S-4700 Hitachi scanning electron microscope (SEM). Six micro-liters of molten agarose platinum gel were also dispensed on a carbon coated copper grid. A filter paper was used to wick off the excess material after which the grid was stirred in boiling water to make a thin film of the gel and was investigated by transmission electron microscope (JEOL 1200 EX).

Figure 16:
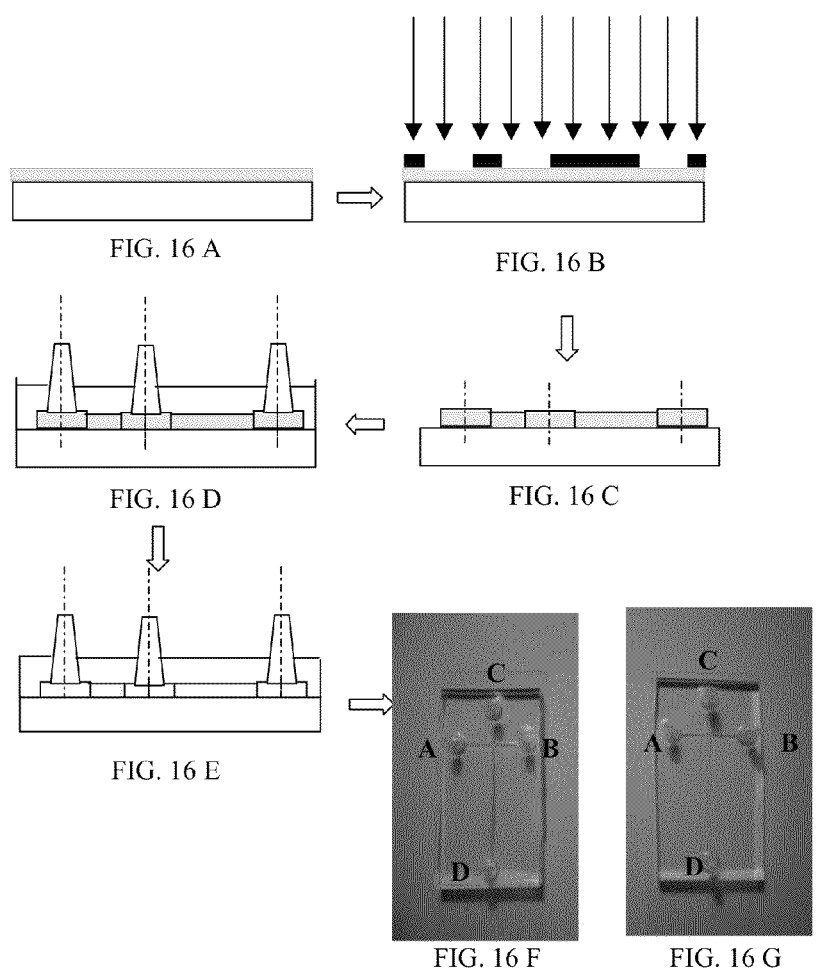
FIG. 16 is a fabrication flow chart. The mold was constructed of poly dimethyl siloxane (yellow, FIG. 16A) and glass (white, FIG. 16A).

Fabrication and Loading of the Glass/PDMS Microchannel Capillaries and DNA Mobility Studies The micro-capillaries were realized in PDMS (poly dimethyl siloxane) and glass using standardized soft lithography and replica molding processes (as described in D. C. Duffy, J. C. McDonald, J. A. Schueller, G. M. Whitesides, *Anal. Chem.* 70, 4974 (1998) and incorporated herein by reference). The separation channels molded in PDMS using a SU-8 mold were 225 micron (thick)×1000 micron (wide)×25.40 mm (long) and had a taper of 500 micron in an inch. The PDMS microchannels were irreversibly sealed to another clean glass substrate after both surfaces were exposed to oxygen plasma. FIG. 16 gives a fabrication flowchart for the device. The cross channel "A-B" was used to inject the DNA sample orthogonally into the main separation capillary "C-D" (refer to FIG. 16) and was sealed permanently. Then, the molten agarose with and without platinum nano-particles was injected separately in two different capillaries from the ends C and D thus burying the sample DNA trapped in between channels A-B and C-D as a plug. The gel is allowed to cool off within the capillary in this condition. Two platinum wires were inserted into the inlet/outlet ports of the separation capillary as electrodes and a high voltage DC power supply was connected to them. The chip was mounted on a UV trans-illuminator and a Kodak digital camera interfaced with a computer was used for imaging purposes. The voltage applied through the platinum wires size fractionated a 1 kbp DNA ladder (M/S promega) within a plain agarose filled capillary. The horizontal distance of traverse of the DNA stains inside the capillary was measured and the time of its movement was recorded. The one-dimensional mobility model for the DNA stains was applied in these capillaries. Simultaneously the mobilities were observed in standardized slab gels using the same setup and the stain mobility was studied in the agarose gel doped with highest platinum concentration (11.6 mM) and plain agarose samples. The mobilities are enhanced 1.5 fold in the new gel samples.

Example 1

Nano-Particle Doped Agarose Gel Analysis

Metal nano-particles can significantly alter electrical properties of various polymers and other materials. To determine if nano-particles may enhance the conductivity of separation matrices, the electrical properties of platinum nano-particle doped agarose were analyzed.

Figure 1B:
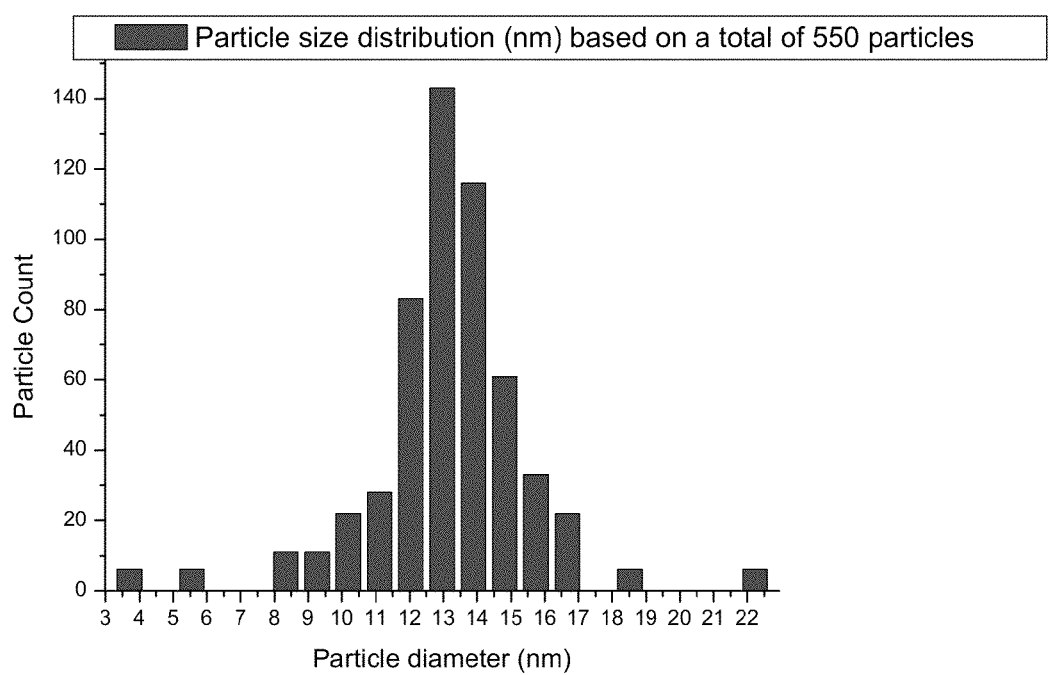
FIG. 1B shows a histogram for the particle size distribution of the platinum nano-particles employed in one embodiment of the inventive gel material.
Figure 2A:
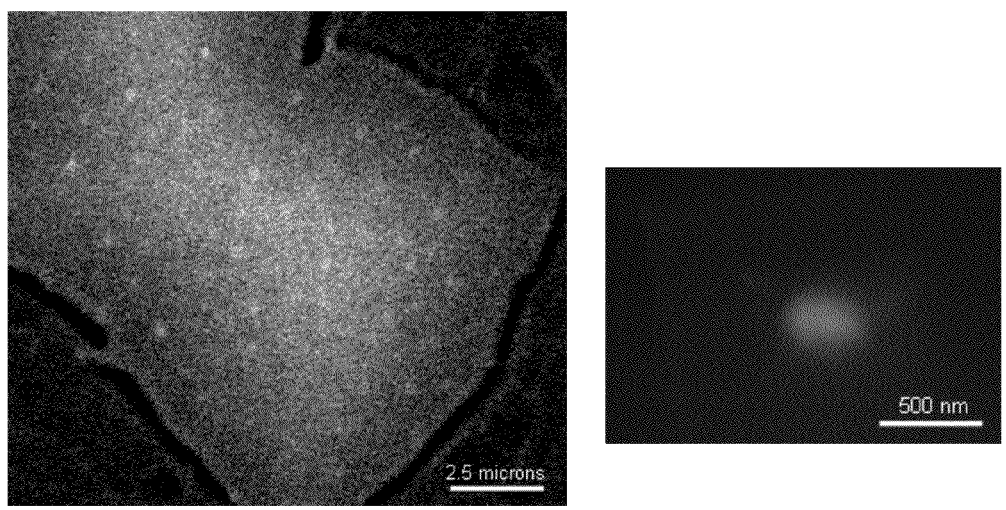
FIG. 2A shows array of platinum nano-particles in agarose matrix in a field emission scanning electron microscope.
Figure 3:
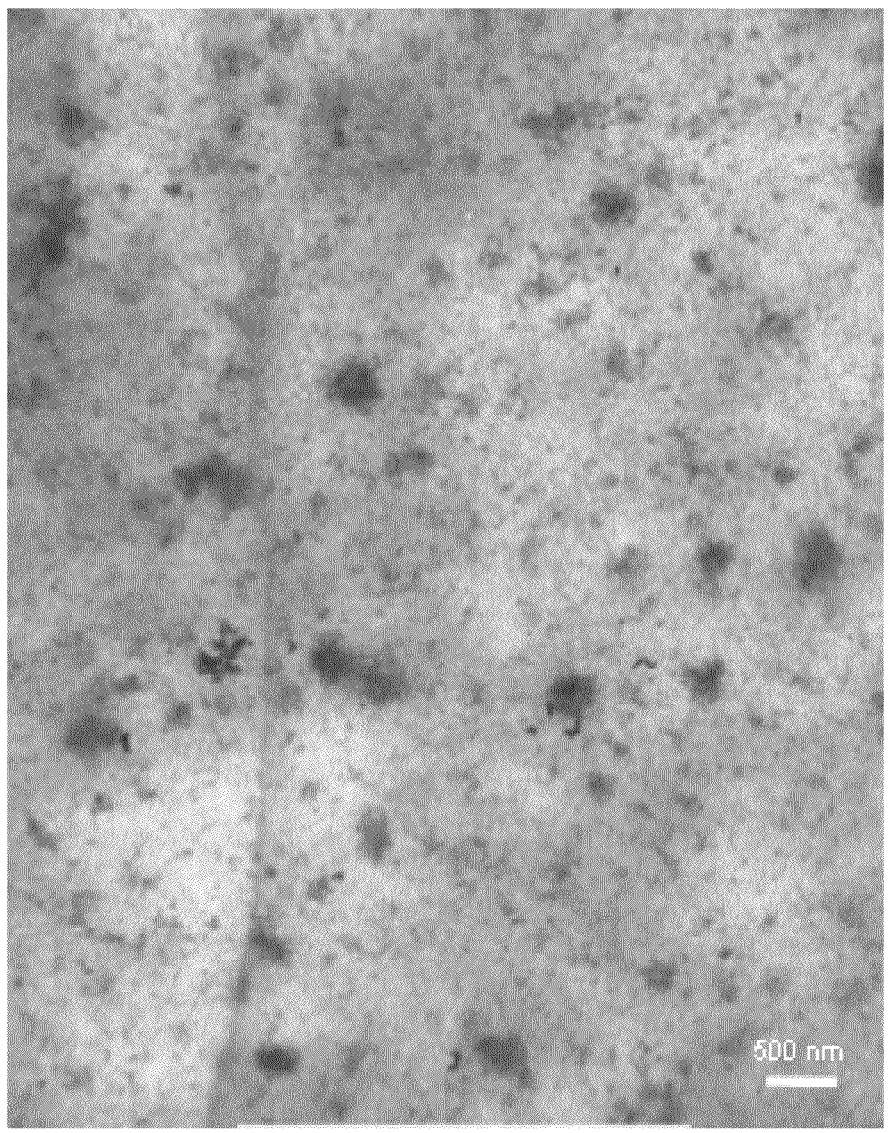
FIG. 3 is a TEM image of the inventive agarose-platinum composite, according to one embodiment.
Figure 4:
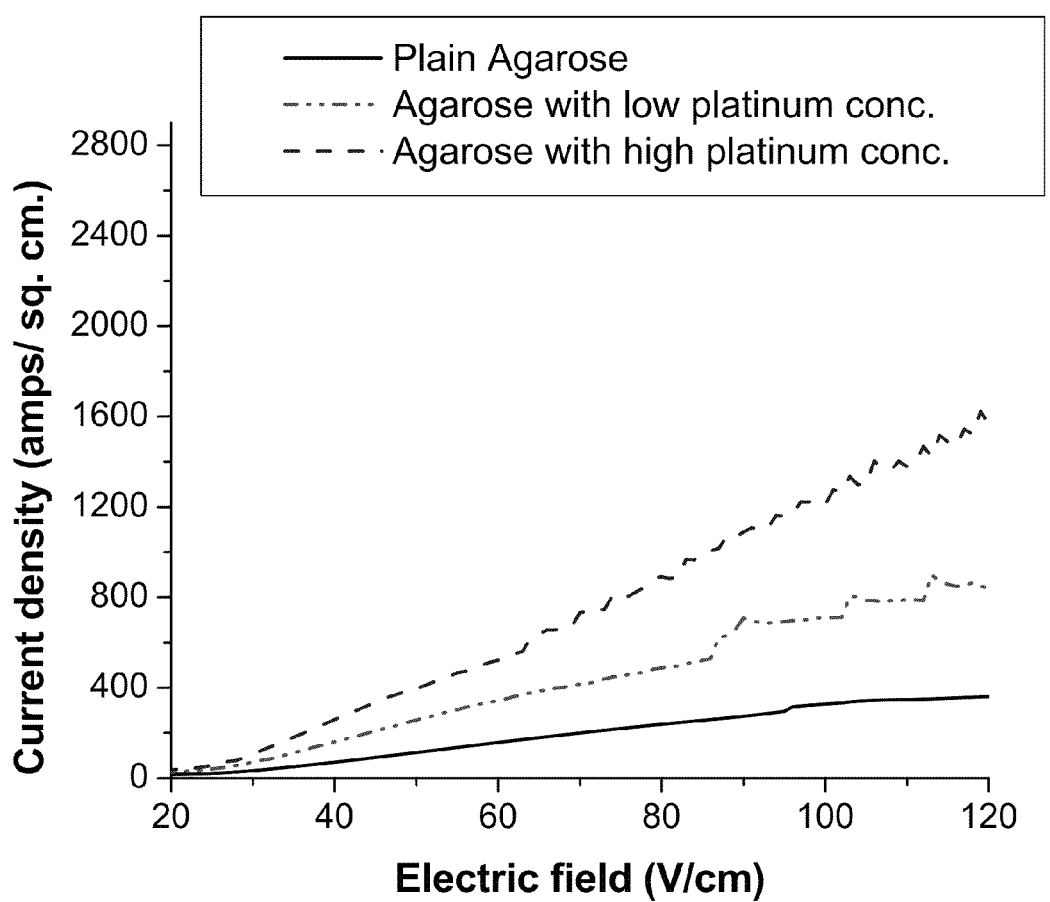
FIG. 4 is a plot between current density and electric field of the tests and comparisons between the agarose and the inventive agarose-platinum composition (with two platinum concentrations).
Figure 14:
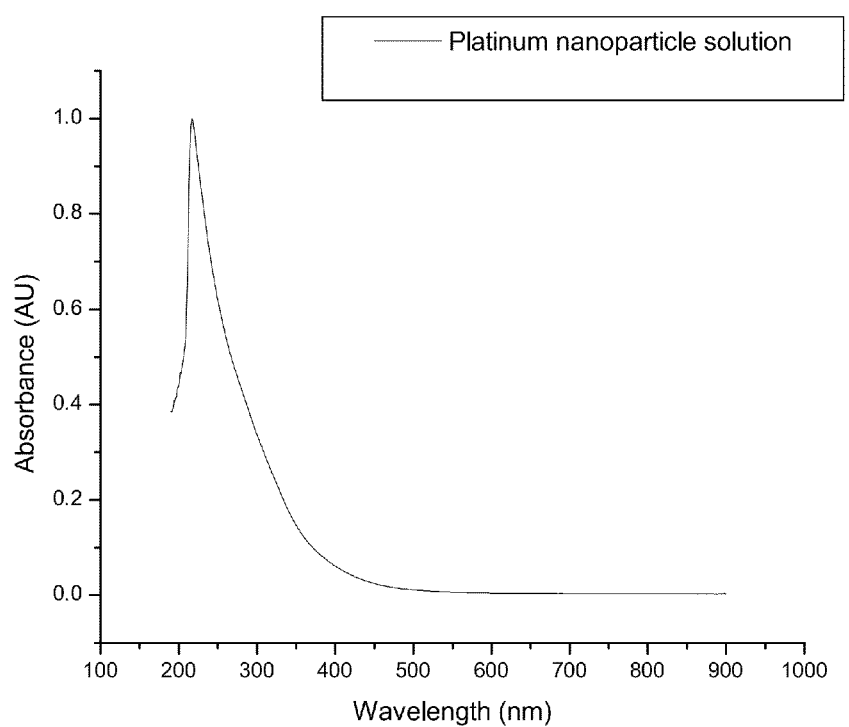
FIG. 14 graphically depicts the UV-Vis absorbance spectra of platinum hydrosol.
Figure 15A:
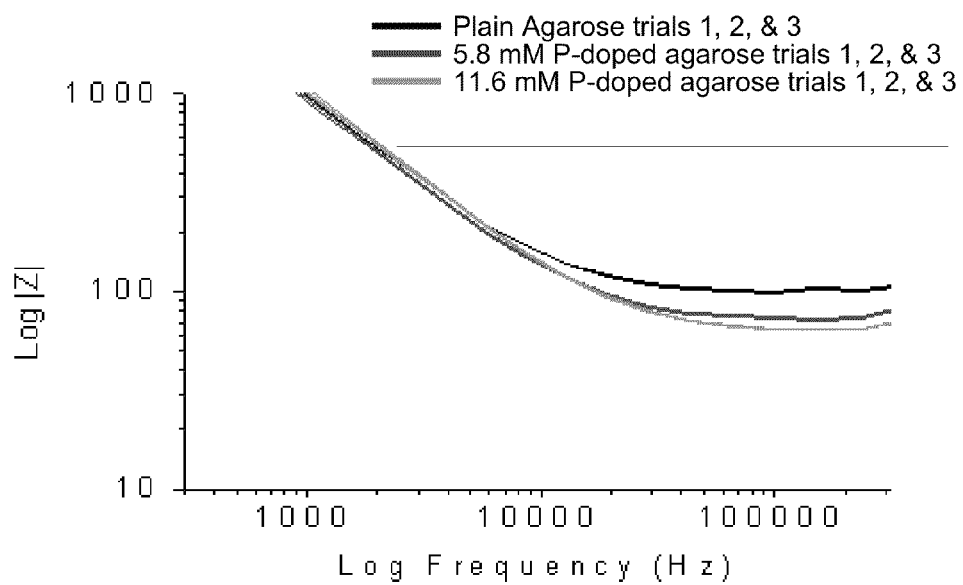
FIG. 15 shows logarithmic plots of a modulus of impedance with frequency (FIG. 15A) and of phase angle with frequency (FIG. 15B).
Figure 15B:
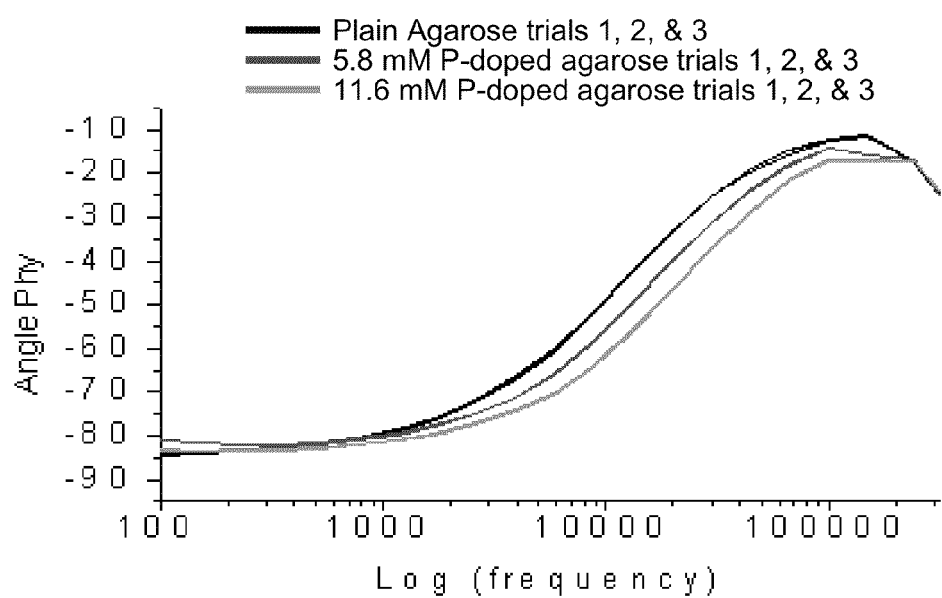

Platinum nano-particles for doping the agarose gels were prepared as hydrosols of two different platinum concentrations by sodium boro-hydride reduction of potassium tetrachloroplatinate with mercapto-succinic acid as a surface-protecting group. UV-Vis absorbance spectra of the platinum hydrosols (FIG. 14) gave a sharp peak in the 216 nm region consistent with the presence of platinum nano-particles. TEM showed the formation of spherical platinum nano-particles with a mean diameter of 13±4 nm (FIGS. 1A and 1B). Platinum-doped 2% agarose gels were prepared by heating agarose powder in a 1:4 volumetric ratio mixture of 1×TAE buffer and platinum hydrosol. Thin films of the doped gel were spun-coated onto glasssubstrates and examined by field emission scanning electron microscopy (FESEM,) (FIG. 2A). A well-distributed array of platinum nano-particles (200-250 nm) buried inside the agarose matrix was visualized and characterized by electron dispersive spectroscopy (FIG. 2B). The high peak around 2.09 KeV obtained from the "M__ platinum lines" indicated a strong presence of platinum metal. The absence of the PtCl peak at 2.62 KeV indicated the complete reduction of the chloroplatinate salt. The particle aggregation observed in the agarose-platinum films was a result of the microwave heating process. TEM micrographs of a thin section of gel showed a range of platinum particle sizes from the large aggregates observed in the SEM down to approximately 10 nm particles distributed throughout the matrix (FIG. 3).

Figure 6:
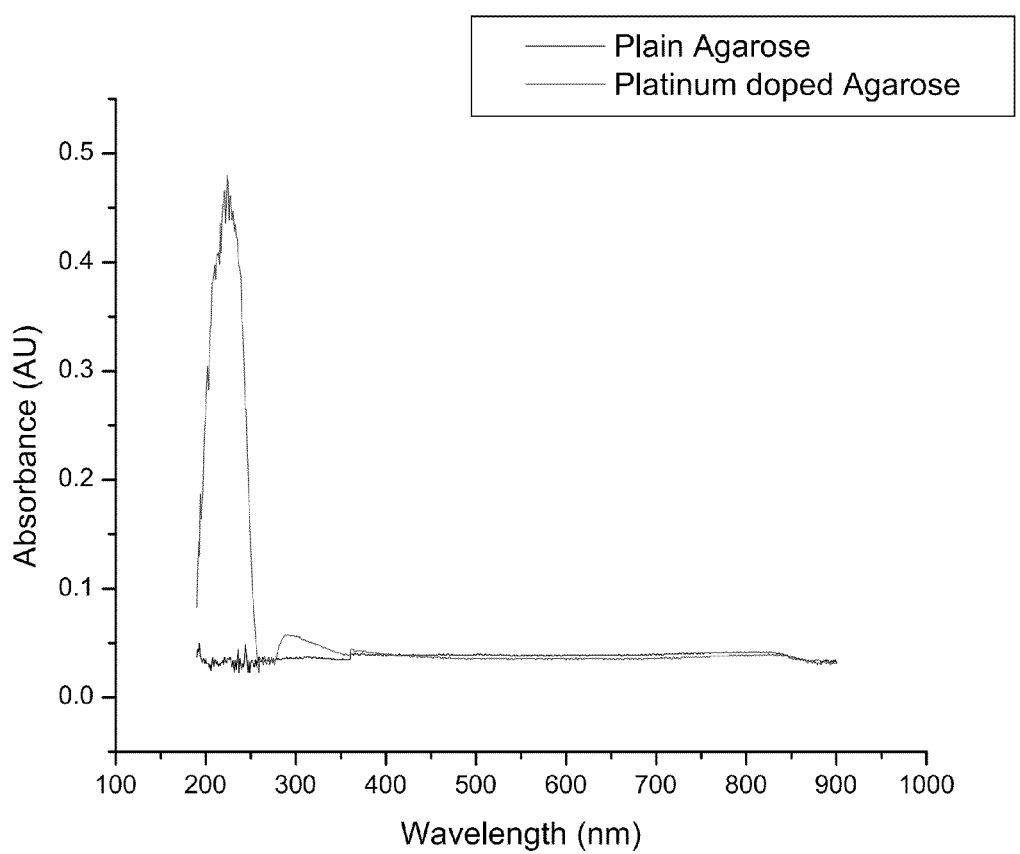
FIG. 6 shows UV-Vis absorption spectra of the agarose gel and the inventive agarose-platinum gel composite.

An UV-Vis absorbance spectra was also performed on the agarose-platinum composite, as shown in FIG. 6, where a sharp peak at 216 nm is found for all platinum dispersions which can be attributed to the presence of Pt nano-particles in the composite. Another smaller shoulder near 300 nm was observed due to the presence of platinum particle aggregates. The agarose-platinum curve shows a broadened shoulder strongly suggesting the occurrence of coagulated particles in the agarose matrix. A similar feature was observed in the TEM image of the agarose platinum films, which demonstrates a much smaller presence of platinum aggregates over the mono-dispersed phase.

In summary, agarose may be doped with platinum nano-particles by using a platinum hydrosol made using sodium boro-hydride reduction of potassium tetra-chloroplatinate with mercapto-succinic acid.

Example 2

DNA Migration Analysis

Advances in nucleic acid electrophoresis have provided an overall reduction in the size of apparatus, reduction in use of reagents, and increased separation speed. However, these advances remain limited due to voltage requirements that can be as high as 10-30 kV. To determine if nano-particles can enhance the separation of nucleic acids in a separation matrix at low voltage, platinum doped agarose gels were analyzed.

DNA segments were size-fractionated on doped and undoped gels at 200, 150, 100, and 50 volts. An enhancement in the segment mobility was observed on the platinum nano-particle doped gels. For example, FIG. 7 shows a time sequence for the electrophoresis of a 527 bp segment on plain agarose and platinum doped agarose (higher concentration hydrosol) gels at a DC potential of 200 V. Similar images were taken at 150, 100, and 50 volts. A more rapid migration was observed on the doped gels.

Figure 8:
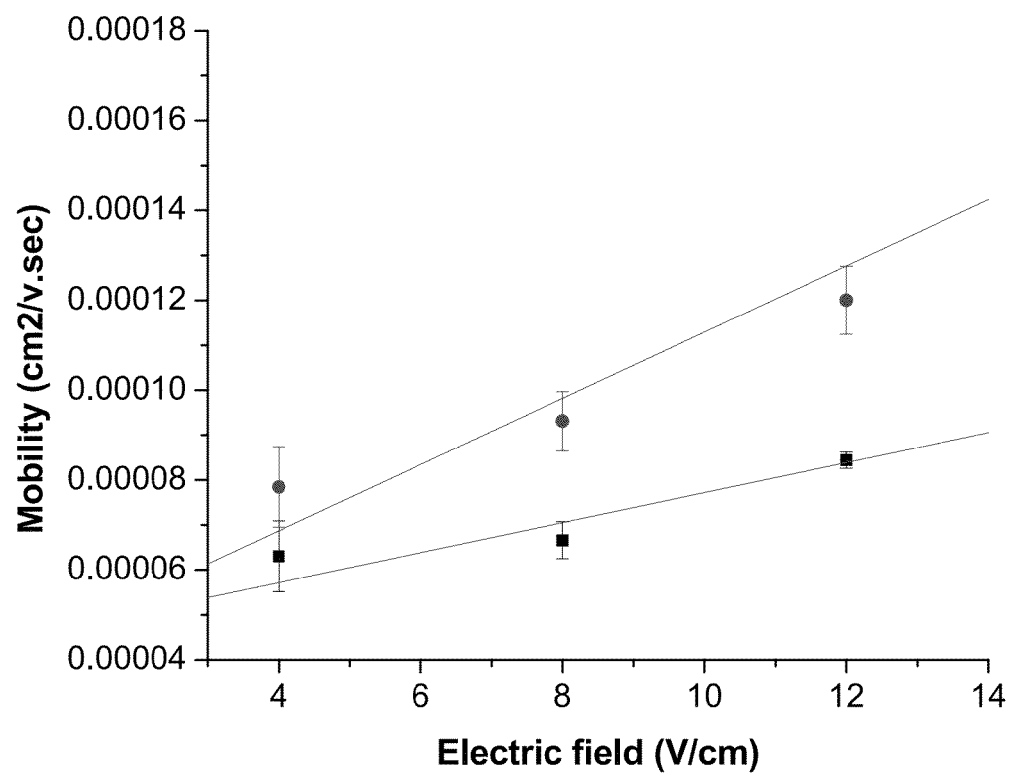
FIG. 8 shows mobility plats of DNA on the agarose gel and the agarose-platinum gel.
Figure 9A:
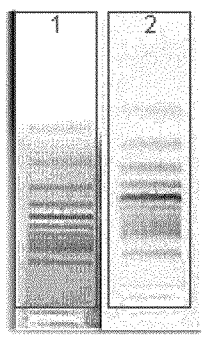
FIG. 9 shows an Image J analysis for studying band broadening effects between images of both plain agarose (FIG. 9A, lane 1) and nano-particle doped agarose (FIG. 9A, lane 2).
FIG. 9B graphically illustrates an analysis comparing the band sizes of plain agarose and nanoparticle doped agarose.
Figure 9B:
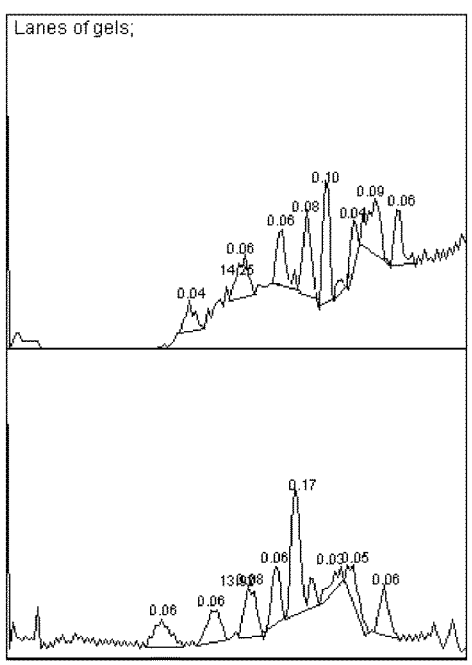

The mobility values of the DNA stains were calculated using the one dimensional mobility equation ($\mu=v/E$), where, $\mu$=mobility of the stain, v=velocity (cm/sec.), E=electric field (V/cm). The mobility values were plotted with the electric field in FIG. 8 for both the doped and undoped gels. An increase in the mobility of the DNA was observed for the doped gel resulting in a mobility increase from $6.6 \times 10^{-5}$ cm$^2$/Vsec to $9.3 \times 10^{-5}$ cm$^2$/Vsec (1.5 times) (Electric Field=8 V/cm) from undoped to doped gel using a standard gel electrophoresis method. At fields below this, the mobility of different DNA strands did not show any remarkable difference in either gel type. The difference in mobility values increase at higher field values of 16 V/cm. The increased mobility does not affect the resolving power of the gel. This is shown by electrophoresis of a 100-1000 bp gene marker on the doped gel (FIG. 9), which showed no change in resolution from the undoped gel.

Figure 5:
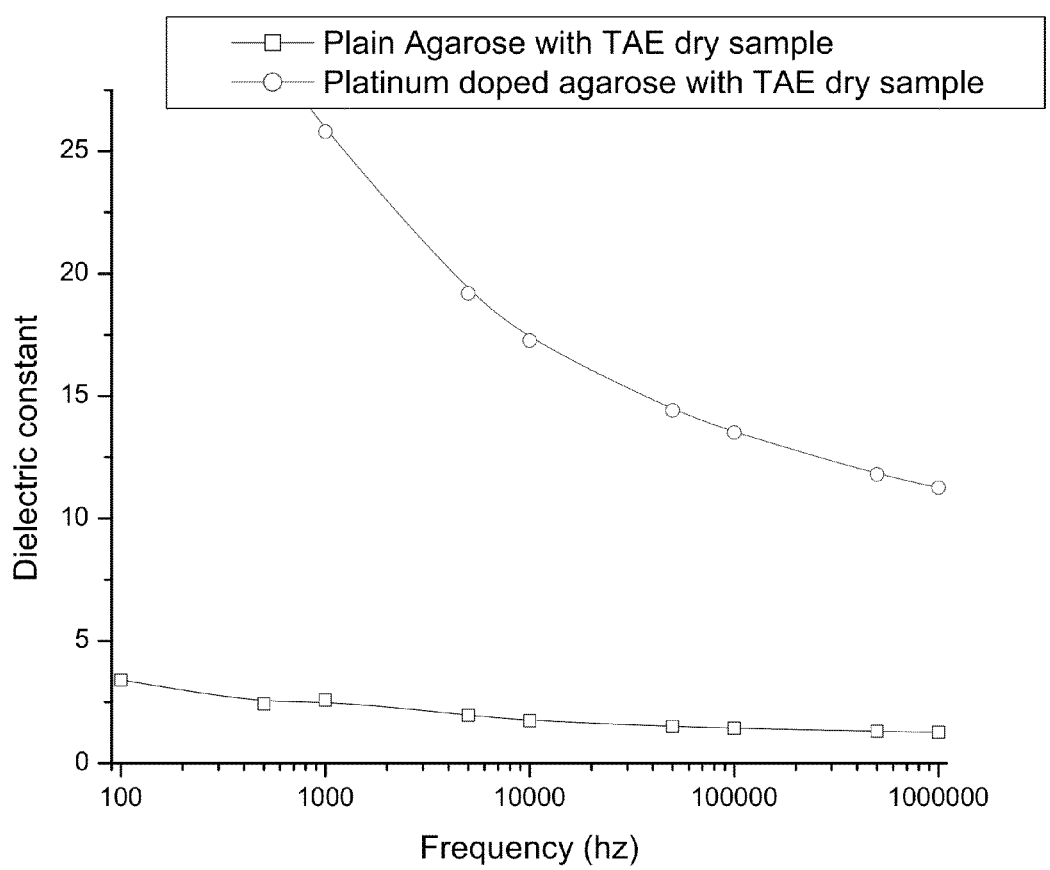
FIG. 5 shows a comparison of the dielectric constant of the agarose gel and the inventive agarose-platinum gel composite.
Figure 10:
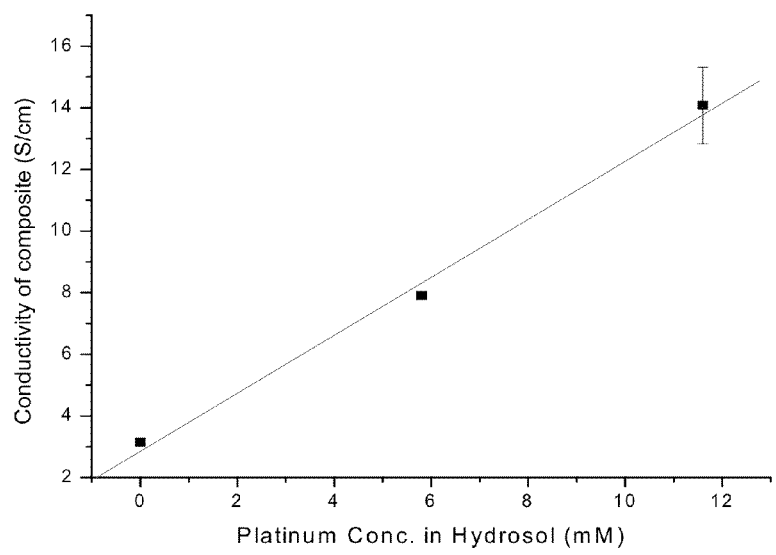
FIG. 10 graphically depicts a plot between gel conductivity (S cm$^{-1}$) and platinum concentration in the hydrosol (mM) used to prepare the gel.
Figure 13A:
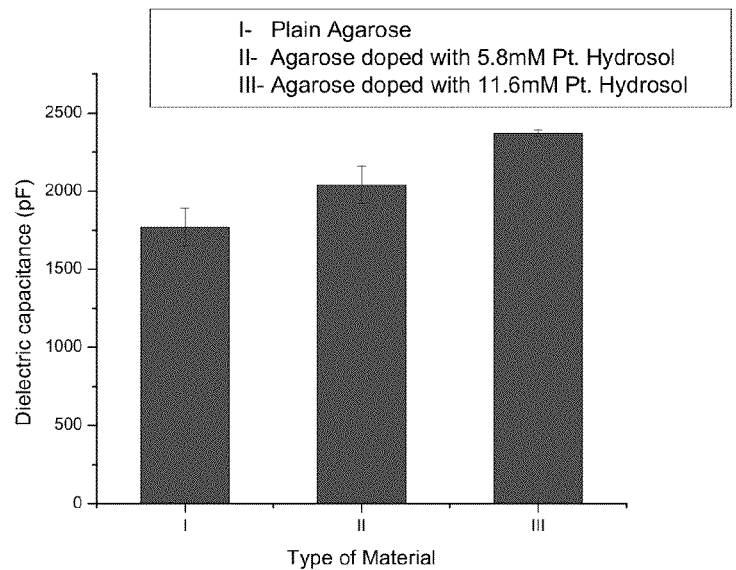
FIG. 13A depicts the comparison of gel dielectric capacitance for plain agarose (I), agarose doped with 5.8 mM of platinum hydrosol (II) and agarose doped with 11.6 mM of platinum hydrosol (III).
Figure 13B:
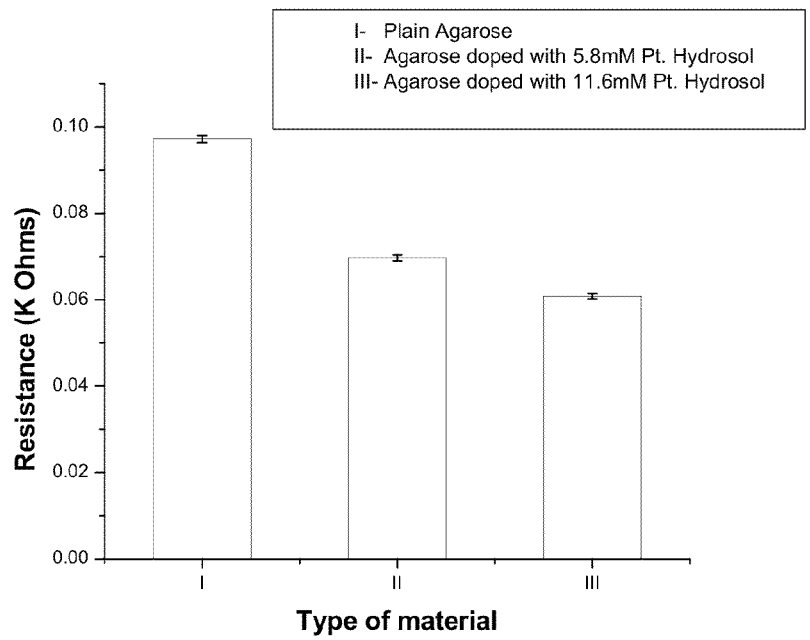
FIG. 13B shows the comparison of gel resistance for data obtained on plain agarose (I), agarose doped with 5.8 mM of platinum hydrosol (II) and agarose doped with 11.6 mM of platinum hydrosol (III). Data was obtained by a parameter extraction method.

The cause of the mobility increase was investigated by analyzing the electrical properties of doped and undoped gels. Current-voltage (IV) measurements indicated an average bulk conductivity of the undoped agarose film of 3.15 S cm$^{-1}$, which changed to 7.2 S cm$^{-1}$ and 14.07±1.24 S cm$^{-1}$ respectively, on doping with the low and high concentration platinum hydrosols. A plot of the conductivity against the platinum concentration shows an approximately linear relationship (FIG. 10). Impedance spectroscopy was performed on the different gel materials and a decrease of the characteristic impedance in the range of 100 Hz-100 kHz was observed (FIG. 5). The corresponding range, where the bulk solution resistance dominates (and where it was lower) was also shifted to a higher frequency, which was attributed to an increase in ionic concentration. FIG. 12 provides a summary of the average of $R_s$ and $C_{di}$. The solution resistance decreased from about 97.2±0.8 ohms to about 60.8±0.6 ohms, which was about a 37% decrease (FIG. 13). This increased conductivity of the doped gels could have arisen from the NaCl and KCl salts that are co-products in the platinum hydrosol synthesis (increased conductivity due to increased ionic strength). However, this should have resulted in reduced DNA mobility due to the screening of DNA molecules by an increase in counter-ions in the surrounding ion atmosphere. Increased electrophoretic mobility in the platinum doped gels can be explained by the dielectric constant enhancement as per the equation, $\mu = \in \in_0 \zeta / \eta$ where, $\mu$=mobility of the ion, $\in$ is the dielectric constant of the medium, $\zeta$ is the zeta-potential of the ion and $\eta$ is the viscosity of the medium.

Nano-particles of metals have been used for increasing E of polymer films as described in K. Naka, H. Itoh, S. Y. Park, Y. Chujo, *Polymer Bulletin*, 52, 171 (2004). The isolated metal nano-particles become polarized due to the presence of an applied electric field, thus enhancing the $\in$ value of the medium. The constant nature of the difference at higher frequencies can be attributed to the inability of the dipoles to align with the changing electric field. The higher a value can be attributed to an overall change in the background dielectric constant (real part of $\in$) due to the effective medium theory. FIG. 5 shows the frequency vs. dielectric constant ($\in$) comparison for the agarose (open squares) and the platinum agarose composite (open circles). The difference between the two curves is more prominent at lower frequencies. A comparison of the $\in$ values was made at 1 KHz. For the plain agarose the a value was obtained as 2.4. After doping with the highest concentrated platinum solution, the a value changed to 19.2, about 8 times higher. Also, the $\in$ value of the composite material is higher than either of the constituents, which was from quantum effect introduced by the dispersed phase.

The viscosity of the medium typically depends on the percentage of agarose, which remains unaltered in our case in both plain and doped agarose. The DNA molecule, being highly negatively charged, does not have an alteration in its zeta potential value because of a change in surrounding ion atmosphere. Therefore, the increased mobility may be attributed to the enhancement of dielectric constant. The slope of the plot of mobility versus electric field doubles in case of the doped agarose showing possibility of capillary electrophoresis at lower electric field values. The newly formed gel samples were fractionated in micro-fabricated capillaries and their electrophoresing voltages were recorded. Several different agarose concentrations ranging from 1.0 to 2.5% were used. The agarose took excess curing times at lower concentrations and had a greater chance of bubble formation disrupting the separation process. At higher concentrations (2.5%), the gelling time was very short as compared to the loading time and thus the capillary was discontinuously filled and did not show any electrophoretic behavior. Concentrations between 1.5 to 2% (by weight) were found to be effective in demonstrating separation repeatedly. Also, various operating voltages were used for checking the size separation and 300 V (Electric field=85-100 V/cm) was found to be sufficient for electrophoresing the sample. No substantial electrophoresing effects below this voltage were found. A plug like movement of a 100-1000 bp gene marker was observed (FIG. 17A picture taken at the end of 25 seconds) for approximately 45 secs. This was followed by the size fractionation immediately at the end of 50 seconds (FIG. 17B). A mobility analysis of the marker during the plug like behavior of the stain was performed and the mobility was calculated as 9.101E-4 cm2/Vsec. (Stain velocity=0.078 cm/sec., Electric field=85.7 V/cm).

A 750 bp segment was also electrophoresed using similar capillaries and the mobility was (7.84+0.2)E-4 cm2/V sec. (FIG. 18A). The stain was formulated by using an external voltage of 65 V (corresponding to an electric field of 25 V/cm). The polarity of the electrodes was changed and the stain was further moved in the reverse direction at the same operating voltage (FIGS. 18B and 18C). This high mobility value of the 100-1000 bp ladder can be attributed to the contribution of the smaller segments of DNA present in the injected volume. Shorter segments move faster than the longer segments in any conventional electrophoresis process. In the case of the 750 bp segment, the entire injected volume of the sample contained a higher segment length (750 bp). The ladder was comprised of different sizes (most of them less than 750 bp) and, thus, the overall mobility increased (consider a weighted average of the individual stain mobilities of all segments 100-1000 bp) during the plug like motion.

In summary, the nano-platinum agarose composite material had enhanced sample mobility and increased conductivity. The sample mobility in the composite increased from 6.6 E-5 cm$^2$/V·sec to 9.3 E-5 cm$^2$/V·sec (1.5 times) at low (8V/cm) field values. The slope of the mobility versus electric field characteristics increased by a factor of 2, whereas the conductivity of the new composite was found to increase 3-4 fold. The mobility increase was due to a decreased gel resistance (37%) and an increase in the dielectric constant of the medium (1.34 fold). This novel gel material has been used to perform low voltage capillary electrophoresis in glass PDMS micro-channels using 25V/cm electric field and 65V external voltage.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

We claim:

1. A method of separating nucleic acids comprising:
   a. mixing a platinum nano-particle dispersion in a buffer resulting in a nano-buffer suspension, wherein the nano-particle sizes range from about 3 to 22 nm;
   b. mixing separation matrix powder in the nano-buffer suspension;
   c. heating the separation matrix-nano-buffer suspension until the matrix is melted;
   d. cooling the separation matrix-nano-buffer suspension until the matrix is gelled, wherein the cooled separation matrix does not exhibit an absorbance peak within the wavelength range of 450 nm to 600 nm;
   e. loading nucleic acid samples into the gelled matrix; and,
   f. electrophoresing the nucleic acid samples into the gelled matrix at a low voltage, wherein the electric field is less than about 200 V/cm.

2. The method of claim 1, wherein the nano-buffer suspension has a pH between about 8.4 and about 8.6.

3. The method of claim 1, wherein the separation matrix is selected from the group consisting of agarose, polyacrylamide, hydroxyalkeylcellulose, polyvinyl alcohol, and mixtures thereof.

* * * * *